United States Patent [19]

David

[11] Patent Number: 4,798,701
[45] Date of Patent: Jan. 17, 1989

[54] METHOD OF SYNTHESIZING AMORPHOUS GROUP IIIA-GROUP VA COMPOUNDS

[75] Inventor: Lawrence D. David, Wappingers Falls, N.Y.

[73] Assignee: International Business Machines Corporation, Armonk, N.Y.

[21] Appl. No.: 72,486

[22] Filed: Jul. 13, 1987

[51] Int. Cl.$^4$ .................. C22C 28/00; C22C 21/00; C01B 25/08; C01B 21/06
[52] U.S. Cl. .................... 420/528; 420/555; 420/576; 420/579; 423/289; 423/290; 423/299; 423/409; 423/412
[58] Field of Search ............. 420/528, 555, 576, 579, 420/345; 423/289, 290, 299, 409, 412, 344, 659; 156/DIG. 70, 613

[56] References Cited

U.S. PATENT DOCUMENTS

| | | | |
|---|---|---|---|
| 4,141,778 | 2/1979 | Domracheu et al. | 156/613 |
| 4,250,205 | 2/1981 | Constant et al. | 156/613 |
| 4,312,970 | 1/1982 | Gaul, Jr. | 526/279 |
| 4,482,669 | 11/1984 | Seyferth et al. | 524/442 |
| 4,594,264 | 1/1986 | Jensen | 420/579 |
| 4,611,035 | 9/1986 | Brown-Wensley et al. | 423/345 |
| 4,704,444 | 11/1987 | Brown-Wensley et al. | 423/344 |

OTHER PUBLICATIONS

Interrante et al. DTIC Report No. AD-A169 482, May 9, 1986.
Gaskill et al. Appl. Phys. Lett., 48(21), May 26, 1986.
Pitt et al. Organometallics, 5, pp. 1266-1268 (1986).
Wells et al. J. Chem. Soc., Chem. Commun., pp. 487-488 (1986).
Pitt et al. Inorganic Chemistry, 25, pp. 2483-2484 (1986).

Primary Examiner—Gary P. Straub
Attorney, Agent, or Firm—Ira D. Blecker

[57] ABSTRACT

A method of synthesizing amorphous Group IIIA--Group VA compounds. A first solution is prepared which consists of a tris(trialkylsilyl) derivative of either a Group IIIA or Group VA element dissolved in an organic solvent. A second solution is then prepared which consists of a halide of the other of the Group IIIA or Group VA element dissolved in an organic solvent. Then the first and second solutions are mixed such that a Group IIIA-Group VA compound is formed along with a trialkylhalosilane by-product. The final step of the method consists of removing the trialkylhalosilane by-product and organic solvent mixture to form the Group IIIA-Group VA condensed phase.

38 Claims, No Drawings

METHOD OF SYNTHESIZING AMORPHOUS GROUP IIIA-GROUP VA COMPOUNDS

FIELD OF THE INVENTION

This invention relates to the field of organometallic chemistry and, more particularly, relates to the use of organometallic chemistry to synthesize Group IIIA-Group VA compounds.

BACKGROUND OF THE INVENTION

Various Group IIIA-Group VA compounds, such as gallium arsenide, boron nitride, and indium phosphide, are of commercial value to the semiconductor industry. These compounds are often produced by vacuum methods so as to accurately control the purity and stoichiometry of the resultant compounds. Among the most common vacuum methods are sputtering and chemical vapor deposition.

Recently, however, there has been great interest in producing the Group IIIA-Group VA compounds by other methods. Among these other methods is the use of organometallic chemistry to synthesize these compounds. One such organometallic chemical method is metathesis. Metathetical reactions are, of course, not new. For example, Gaul, Jr. U.S. Pat. No. 4,312,970, the disclosure of which is incorporated by reference herein, teaches the preparation of silazane polymers by a metathetical reaction process.

Interrante et al. (DTIC Report No. AD-A169 482, May 9, 1986), the disclosure of which is incorporated by reference herein, teach the production of aluminum nitride powders and thin films via a metathetical reaction. In Interrante et al., trialkylaluminum compounds and ammonia are reacted to form a Lewis acid/Lewis base adduct which thereafter decomposes to aluminum nitride and a gas such as methane. From a practical standpoint, such a reaction is complicated by the use of pyrophoric trialkylaluminum compounds and the production of methane, a flammable gas.

Gaskill et al. (Appl. Phys. Lett., 48 (21), May 26, 1986), the disclosure of which is incorporated by reference herein, teach the preparation of gallium nitride films by the metathesis of trimethylgallium and hydrazine. The principal disadvantage of this process is that hydrazine is explosive and is best avoided if possible.

Others have disclosed the preparation of arsinogallanes. Among these are Pitt et al. (*Organometallics*, 5, p. 1266–1268 (1986)), Wells et al. (*J. Chem. Soc., Chem. Commun.*, p. 487–488 (1986)) and Pitt et al. (Inorganic Chemistry, 25, pp. 2483–2484 (1986)), the disclosures of which are incorporated by reference herein. However, these references do not disclose how, or if, one skilled in the art could go from the arsinogallane to gallium arsenide.

Notwithstanding the above efforts, there remains a real need to synthesize Group IIIA-Group VA compounds by organometallic methods.

Accordingly, it is an object of the invention to synthesize Group IIIA-Group VA compounds by organometallic methods.

It is another object of the invention to synthesize Group IIIA-Group VA compounds by organometallic methods which are economical, feasible, and relatively safe.

These and other objects of the invention will become apparent after referring to the following description.

BRIEF SUMMARY OF THE INVENTION

The objects of the invention have been achieved by providing a method of synthesizing amorphous Group IIIA-Group VA compounds which is economical, feasible and relatively safe.

One aspect of the invention relates to forming a first solution of a tris(trialkylsilyl) derivative of a Group IIIA element dissolved in an organic solvent. The Group IIIA element is selected from the group consisting of aluminum, boron, gallium, indium, and mixtures thereof. A second solution is then formed of a halide of a Group VA element dissolved in an organic solvent. The Group VA element is selected from the group consisting of antimony, arsenic, nitrogen, phosphorous, and mixtures thereof. Then the first and second solutions are mixed such that a Group IIIA-Group VA compound is formed along with a trialkylhalosilane by-product. The final step of the method comprises removing the trialkylhalosilane by-product and organic solvent mixture to form the Group IIIA-Group VA condensed phase.

A second aspect of the invention relates to a method of synthesizing an amorphous Group IIIA-Group VA compound which comprises the steps of forming a first solution of a tris(trialkylsilyl) derivative of a Group VA element in an organic solvent. The Group VA element is selected from the group consisting of antimony, arsenic, nitrogen, phosphorus, and mixtures thereof. A second solution is formed comprising a halide of a group IIIA element dissolved in an organic solvent. The Group IIIA element is selected from the group consisting of aluminum, boron, gallium, indium, and mixtures thereof. The process further comprises mixing the first solution with the second solution so that a reaction occurs wherein a Group IIIA-Group VA compound and a trialkylhalosilane by-product are produced. Thereafter the process comprises removing the trialkylhalosilane by-product and organic solvent mixture to form the Group IIIA-Group VA condensed phase.

DETAILED DESCRIPTION OF THE INVENTION

According to the invention there is disclosed a method of synthesizing amorphous Group IIIA-Group VA compounds. The method comprises the steps of, firstly, mixing equimolar amounts of a tris(trialkylsilyl) derivative of a Group IIIA element with a halide of a Group VA element in an organic solvent system. The Group IIIA element is selected from the group consisting of aluminum, boron, gallium, indium, and mixtures thereof and the Group VA element is selected from the group consisting of antimony, arsenic, nitrogen, phosphorus, and mixtures thereof.

The organic solvent may be, by way of illustration and not by way of limitation, tetrahydrofuran (THF), decalin, dioxane, hexane, octane, benzene, xylene, or toluene. No protic solvents such as water or ethanol or solvents with active hydrogens such as acetone, 2-butanone or DMSO will work. With the teaching provided by this application the proper organic solvent may be chosen by those skilled in the art.

The next step in the method comprises reacting the components of the mixture of the first step to form an adduct of the general formula

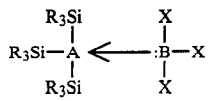

wherein
R = an alkyl group;
A = aluminum, boron, gallium, indium, or mixtures thereof;
B = antimony, arsenic, nitrogen, phosphorus, or mixtures thereof; and
X = bromine, chlorine, fluorine, or iodine.

As is apparent a Lewis acid/Lewis base adduct is formed. Thereafter a Group IIIA-Group VA compound having the general formula AB is formed as well as a halide by-product having the general formula $R_3SiX$ (trialkylhalosilane). Thus, the A and B components have reacted by metathesis.

A final step of the method comprises removing the $R_3SiX$ halide by-product to form the AB stoichiometric condensed phase. As will become apparent, this step may be readily accomplished by distillation.

The condensed phase thus formed may then be dried in nitrogen or another inert gas and then heated to remove any residual solvent and volatiles.

As the tris(trialkylsilyl) derivatives are pyrophoric it is necessary to maintain certain conditions during processing of the mixture. It is necessary that the solvent and all apparatus used to process the mixture be dried and deoxygenated. Such precautions are commercially feasible. With these precautions the Group IIIA-Group VA compounds may be easily synthesized in a relatively safe manner.

In principle, any alkyl group should work; it is preferred, however, that the alkyl group may be selected from the group consisting of methyl, ethyl, propyl, and butyl groups. Most preferably, the alkyl group should be the methyl group since the trimethylhalosilane is more volatile and thus easier to distill than any of the other trialkylhalosilanes.

More generally, the method according to the invention of synthesizing amorphous Group IIIA-group VA compounds comprises the following steps. A tris(trialkylsilyl) derivative of a Group IIIA element is dissolved in a dried, deoxygenated organic solvent to produce a first solution. The Group IIIA element is selected from the group consisting of aluminum, boron, gallium, indium, and mixtures thereof. Then a halide of a Group VA element is dissolved in another dried, deoxygenated solvent to produce a second solution. The Group VA element is selected from the group consisting of antimony, arsenic, nitrogen, phosphorus, and mixtures thereof. Then the first and second solutions are mixed wherein a reaction occurs such that a Group IIIA-Group VA compound and a trialkylhalosilane by-product are produced in the organic solvent mixture. Finally, the method comprises removing the trailkylhalosilane by-product and organic solvent mixture to form a Group IIIA-Group VA condensed phase.

The alkyl group may be selected as indicated above.

The step of removing may be conveniently accomplished by distillation. Again, the Group IIIA-Group VA condensed phase so formed may then be dried in nitrogen or some other inert gas and heated (i.e. roasted or calcined) to form the amorphous Group IIIA-Group VA compound.

The Group IIIA-Group VA compounds so produced may subsequently be used as a raw material feed for crystal growth by conventional crystal pulling techniques. The compounds can also be annealed and processed in their amorphous state for use as, for example, thin films.

The Group IIIA-Group VA compounds synthesized by this method may include aluminum nitride, aluminum phosphide, boron nitride, boron phosphide, gallium arsenide, gallium phosphide, gallium nitride, indium phosphide, indium arsenide, and indium antimonide. Of these compounds the only ones that are dangerous to produce are the nitrides in that the nitrogen halide used in the method can be explosive. However, under the proper operating conditions the nitrides may even be produced in a safe manner.

It should be understood that the amorphous compounds produced according to the methods of the invention shall also include compounds which are substantially amorphous as defined by the presence of about 10% or less by volume of crystalline phases. For some applications, this small amount of crystallinity would not be detrimental to the end use of the compound. On the other hand, for some applications such as where the compound is to be used as a raw material feed for the growth of single crystals, it is preferred that the amorphous compound be entirely amorphous, i.e., possessing zero crystallinity, as characterized by the absence of any lines in an X-ray diffraction pattern. Therefore, whenever throughout this specification the term 'amorphous' is used, it should be understood to include 'substantially amorphous' as well.

According to the invention a further method is disclosed of synthesizing amorphous Group IIIA-Group VA compounds which comprises the following steps. The first step comprises mixing equimolar amounts of a tris(trialkylsilyl) derivative of a Group VA element with a halide of a Group IIIA element in an organic solvent system. The Group VA element is selected from the group consisting of antimony, arsenic, nitrogen, phosphorus, and mixtures thereof. The Group IIIA element is selected from the group consisting of aluminum, boron, gallium, indium, and mixtures thereof.

As before the solvents suitable for use in the invention include by way of illustration and not by way of limitation THF, decalin, dioxane, hexane, octane, benzene, xylene, and toluene.

In the next step of the method of components of the mixture just described are reacted to form a Lewis acid/Lewis base adduct having the general formula wherein

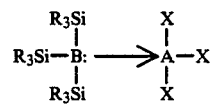

wherein
R = an alkyl group;
B = antimony, arsenic, nitrogen, phosphorus, or mixtures thereof;
A = aluminum, boron, gallium, indium, or mixtures, thereof; and
X = bromine, chlorine, fluorine, or iodine.

Thereinafter a Group IIIA-Group VA compound is formed having the general formula AB and a halide by-product is also produced having the general formula R$_3$SiX (trialkylhalosilane). As is apparent the Group IIIA-Group VA compound has again been formed by metathesis.

A final step of the method comprises removing (e.g. by distillation) the R$_3$SiX by-product to form the AB stoichiometric condensed phase.

The condensed phase can then be dried and heated to form the amorphous Group IIIA-Group VA compound.

As described previously, the alkyl group is preferably selected from the group consisting of methyl, ethyl, propyl, and butyl groups. The most preferred alkyl group is the methyl group.

More generally, the method of synthesizing amorphous Group IIIA-Group VA compounds comprises the following steps. A tris(trialkylsilyl) derivative of a Group VA element is dissloved in a dried, deoxygenated organic solvent to produce a first solution. The Group VA element is selected from the Group consisting of antimony, arsenic, nitrogen, phosphorus, and mixtures thereof. Then a second solution is formed by dissolving a halide of a Group IIIA element in another dried, deoxygenated organic solvent. The Group IIIA element is selected from the group consisting of aluminum, boron, gallium, indium, and mixtures thereof. The first and second solutions are then mixed wherein a reaction occurs such that a Group IIIA-Group VA compound and a trialkylhalosilane by-product are produced in the organic solvent mixture. A final step of the method comprises removing the trialkylhalosilane by-product and organic solvent mixture, such as by distillation, to form the Group IIIA-Group VA condensed phase.

The following compounds may be safely prepared according to this second aspect of the invention: gallium arsenide, gallium phosphide, gallium nitride, indium phosphide, indium arsenide, indium antimonide, aluminum nitride, aluminum phosphide, boron nitride, and boron phosphide.

An interesting aspect of the invention is that any of the Group IIIA-Group VA compounds synthesized according to any method of the invention may be doped during synthesis by varying the starting components. That is, by adding small amounts of a component which represents the dopant, a doped Group IIIA-Group VA compound may be produced. For example, gallium arsenide doped with phosphide or indium phosphide doped with gallium may be synthesized.

The invention will become more apparent after referring to the following examples.

EXAMPLE 1

The reaction apparatus for this and all the following examples is a three-necked round bottom flask fitted with a motor stirrer, a reflux condenser, a heating mantle, a dropping funnel, and gas inlet and outlet. The reactions are to be conducted under dry nitrogen or another dry inert gas. Dissolve 5.79 grams 20.0 mmoles) or tris(trimethylsilyl)gallane, Ga[Si(CH$_3$)$_3$]$_3$, in 250 ml of dried, deoxygenated tetrahydrofuran (THF). Charge a solution of 3.63 grams of arsenic chloride (20.0 mmoles) in 100 ml of dried THF to the addition funnel and then add it dropwise, with stirring, to the gallane solution.

After stirring for 30 minutes at room temperature reflux the solution for six more hours. Cool the solution and then affix a distilling head to the flask in place of the condenser. Reflux the solution again and the trimethylchlorosilane by-product distills off at 58° C. At 67° C. the THF distills off. The distillations cause a powder to precipitate. Separate the powder from the liquid by filtration, dry it in nitrogen, and then roast it in vacuum up to 200° C. to remove the residual solvent and volatiles. This product has a theoretical yield of 2.89 g of amorphous gallium arsenide. The actual yield ranges from 75-95%.

In place of the AsCl$_3$ there can also be substituted AsBr$_3$, AsF$_3$, or AsI$_3$ as the arsenic sources. This changes the distillation by-product to trimethylbromosilane, trimethylfluorosilane or trimethyliodosilane, respectively. Each of these by-products has a differet boiling point so that the solvent must be changed to accommodate these different boiling points. For example, the solvent for AsBr$_3$ may be toluene or decalin, for AsF$_3$ may be THF or hexane and for AsI$_3$ may be xylene or decalin. In any case, the Group IIIA-Group VA compound produced, in this case gallium arsenide, would be the same.

EXAMPLES 2-34

To produce other Group IIIA-Group VA compounds according to the method of Example 1, reference should be made to Table I wherein the starting components for the particular Group IIIA-Group VA product are specified.

TABLE I

| Example No. | Group IIIA Derivative | Group VA Halide | Group IIIA-VA Solvent | Product | By-Product |
|---|---|---|---|---|---|
| 2 | Al[Si(CH$_3$)$_3$]$_3$ | NBr$_3$ | toluene | AlN | (CH$_3$)$_3$SiBr |
| 3 | ↓ | NCl$_3$ | hexane | ↓ | (CH$_3$)$_3$SiCl |
| 4 | ↓ | NI$_3$ | octane | ↓ | (CH$_3$)$_3$SiI |
| 5 | ↓ | PBr$_3$ | toluene | AlP | (CH$_3$)$_3$SiBr |
| 6 | ↓ | PCl$_3$ | hexane | ↓ | (CH$_3$)$_3$SiCl |
| 7 | ↓ | PF$_3$ | THF | ↓ | (CH$_3$)$_3$SiF |
| 8 | ↓ | PI$_3$ | octane | ↓ | (CH$_3$)$_3$SiI |
| 9 | B[Si(CH$_3$)$_3$]$_3$ | NBr$_3$ | toluene | BN | (CH$_3$)$_3$SiBr |
| 10 | ↓ | NCl$_3$ | hexane | ↓ | (CH$_3$)$_3$SiCl |
| 11 | ↓ | NI$_3$ | octane | ↓ | (CH$_3$)$_3$SiI |
| 12 | ↓ | PBr$_3$ | toluene | BP | (CH$_3$)$_3$SiBr |
| 13 | ↓ | PCl$_3$ | hexane | ↓ | (CH$_3$)$_3$SiCl |
| 14 | ↓ | PF$_3$ | THF | ↓ | (CH$_3$)$_3$SiF |
| 15 | ↓ | PI$_3$ | octane | ↓ | (CH$_3$)$_3$SiI |
| 16 | Ga[Si(CH$_3$)$_3$]$_3$ | PBr$_3$ | toluene | GaP | (CH$_3$)$_3$SiBr |
| 17 | ↓ | PCl$_3$ | hexane | ↓ | (CH$_3$)$_3$SiCl |
| 18 | ↓ | PF$_3$ | THF | ↓ | (CH$_3$)$_3$SiF |
| 19 | ↓ | PI$_3$ | octane | ↓ | (CH$_3$)$_3$SiI |
| 20 | ↓ | NBr$_3$ | toluene | GaN | (CH$_3$)$_3$SiBr |
| 21 | ↓ | NCl$_3$ | hexane | ↓ | (CH$_3$)$_3$SiCl |
| 22 | ↓ | NI$_3$ | octane | ↓ | (CH$_3$)$_3$SiI |
| 23 | In[Si(CH$_3$)$_3$]$_3$ | PBr$_3$ | toluene | InP | (CH$_3$)$_3$SiBr |
| 24 | ↓ | PCl$_3$ | hexane | ↓ | (CH$_3$)$_3$SiCl |
| 25 | ↓ | PF$_3$ | THF | ↓ | (CH$_3$)$_3$SiF |
| 26 | ↓ | PI$_3$ | octane | ↓ | (CH$_3$)$_3$SiI |
| 27 | ↓ | AsBr$_3$ | toluene | InAs | (CH$_3$)$_3$SiBr |
| 28 | ↓ | AsCl$_3$ | hexane | ↓ | (CH$_3$)$_3$SiCl |
| 29 | ↓ | AsF$_3$ | THF | ↓ | (CH$_3$)$_3$SiF |
| 30 | ↓ | AsI$_3$ | octane | ↓ | (CH$_3$)$_3$SiI |
| 31 | ↓ | SbBr$_3$ | toluene | InSb | (CH$_3$)$_3$SiBr |
| 32 | ↓ | SbCl$_3$ | hexane | ↓ | (CH$_3$)$_3$SiCl |
| 33 | ↓ | SbF$_3$ | THF | ↓ | (CH$_3$)$_3$SiF |
| 34 | ↓ | SbI$_3$ | octane | ↓ | (CH$_3$)$_3$SiI |

EXAMPLE 35

An alternative method of synthesizing gallium arsenide is described below. In this alternative method, dissolve 14.73 g (50.0 mmoles) of tris(trimethylsilyl)arsine, As[Si(CH$_3$)$_3$]$_3$, 250 ml. of THF. Then add another solution of 8.80 g (50.0 mmoles) of gallium chloride in 100 ml of THF dropwise with stirring, to the arsine solution. The reaction and recovery of the gallium arsenide product then proceeds as in Example 1, yielding a trimethylchlorosilane by-product and 7.0 grams (96.8% of theoretical yield) of amorphous gallium arsenide.

As in Example 1, the GaCl$_3$ may be replaced by GaBr$_3$, GaF$_3$ or GaI$_3$ to produce the gallium arsenide. Representative solvents for those solutions containing GaBr$_3$, GaF$_3$, or GaI$_3$ may be toluene, THF or octane, respectively.

EXAMPLES 36–75

To produce other Group IIIA-Group VA compounds according to the method of Example 35, reference should be made to Table II wherein the starting components for the particular Group IIIA-Group VA product are specified.

TABLE II

| Example No. | Group VA Derivative | Group IIIA Halide | Group IIIA-VA Solvent | Product | By-Product |
|---|---|---|---|---|---|
| 36 | As[Si(CH$_3$)$_3$]$_3$ | GaBr$_3$ | toluene | GaAs | (CH$_3$)$_3$SiBr |
| 37 | ↓ | GaCl$_3$ | hexane | ↓ | (CH$_3$)$_3$SiCl |
| 38 | ↓ | GaF$_3$ | THF | ↓ | (CH$_3$)$_3$SiF |
| 39 | ↓ | GaI$_3$ | octane | ↓ | (CH$_3$)$_3$SiI |
| 40 | P[Si(CH$_3$)$_3$]$_3$ | GaBr$_3$ | toluene | GaP | (CH$_3$)$_3$SiBr |
| 41 | ↓ | GaCl$_3$ | hexane | ↓ | (CH$_3$)$_3$SiCl |
| 42 | ↓ | GaF$_3$ | THF | ↓ | (CH$_3$)$_3$SiF |
| 43 | ↓ | GaI$_3$ | octane | ↓ | (CH$_3$)$_3$SiI |
| 44 | N[Si(CH$_3$)$_3$]$_3$ | GaBr$_3$ | toluene | GaN | (CH$_3$)$_3$SiBr |
| 45 | ↓ | GaCl$_3$ | hexane | ↓ | (CH$_3$)$_3$SiCl |
| 46 | ↓ | GaF$_3$ | THF | ↓ | (CH$_3$)$_3$SiF |
| 47 | ↓ | GaI$_3$ | octane | ↓ | (CH$_3$)$_3$SiI |
| 48 | As[Si(CH$_3$)$_3$]$_3$ | InBr$_3$ | toluene | InAs | (CH$_3$)$_3$SiBr |
| 49 | ↓ | InCl$_3$ | hexane | ↓ | (CH$_3$)$_3$SiCl |
| 50 | ↓ | InF$_3$ | THF | ↓ | (CH$_3$)$_3$SiF |
| 51 | ↓ | InI$_3$ | octane | ↓ | (CH$_3$)$_3$SiI |
| 52 | P[Si(CH$_3$)$_3$]$_3$ | InBr$_3$ | toluene | InP | (CH$_3$)$_3$SiBr |
| 53 | ↓ | InCl$_3$ | hexane | ↓ | (CH$_3$)$_3$SiCl |
| 54 | ↓ | InF$_3$ | THF | ↓ | (CH$_3$)$_3$SiF |
| 55 | ↓ | InI$_3$ | octane | ↓ | (CH$_3$)$_3$SiI |
| 56 | Sb[Si(CH$_3$)$_3$]$_3$ | InBr$_3$ | toluene | InSb | (CH$_3$)$_3$SiBr |
| 57 | ↓ | InCl$_3$ | hexane | ↓ | (CH$_3$)$_3$SiCl |
| 58 | ↓ | InF$_3$ | THF | ↓ | (CH$_3$)$_3$SiF |
| 59 | ↓ | InI$_3$ | octane | ↓ | (CH$_3$)$_3$SiI |
| 60 | N[Si(CH$_3$)$_3$]$_3$ | AlBr$_3$ | toluene | AlN | (CH$_3$)$_3$SiBr |
| 61 | ↓ | AlCl$_3$ | hexane | ↓ | (CH$_3$)$_3$SiCl |
| 62 | ↓ | AlF$_3$ | THF | ↓ | (CH$_3$)$_3$SiF |
| 63 | ↓ | AlI$_3$ | octane | ↓ | (CH$_3$)$_3$SiI |
| 64 | P[Si(CH$_3$)$_3$]$_3$ | AlBr$_3$ | toluene | AlP | (CH$_3$)$_3$SiBr |
| 65 | ↓ | AlCl$_3$ | hexane | ↓ | (CH$_3$)$_3$SiCl |
| 66 | ↓ | AlF$_3$ | THF | ↓ | (CH$_3$)$_3$SiF |
| 67 | ↓ | AlI$_3$ | octane | ↓ | (CH$_3$)$_3$SiI |
| 68 | N[Si(CH$_3$)$_3$]$_3$ | BBr$_3$ | toluene | BN | (CH$_3$)$_3$SiBr |
| 69 | ↓ | BCl$_3$ | hexane | ↓ | (CH$_3$)$_3$SiCl |
| 70 | ↓ | BF$_3$ | THF | ↓ | (CH$_3$)$_3$SiF |
| 71 | ↓ | BI$_3$ | octane | ↓ | (CH$_3$)$_3$SiI |
| 72 | P[Si(CH$_3$)$_3$]$_3$ | BBr$_3$ | toluene | BP | (CH$_3$)$_3$SiBr |
| 73 | ↓ | BCl$_3$ | hexane | ↓ | (CH$_3$)$_3$SiCl |
| 74 | ↓ | BF$_3$ | THF | ↓ | (CH$_3$)$_3$SiF |
| 75 | ↓ | BI$_3$ | octane | ↓ | (CH$_3$)$_3$SiI |

EXAMPLE 76

To produce a doped Group IIIA-Group VA compound, the method of Examples 1 to 34 or 35 to 75 may be used. For purposes of illustration and not of limitation, the components of Example 1 will be modified to synthesize a doped Group IIIA-Group VA compound.

Begin with 5.79 grams (20.0 mmoles) of tris(trimethylsilyl) gallane dissolved in 250 ml of dried, deoxygenated THF. Then, prepare a second solution of 3.61 grams (19.9 mmoles) of AsCl$_3$ plus 13.7 milligrams (0.1 mmole) of PCl$_3$ in 100 ml of THF. Mix the two solutions and process according to the procedure described in Example 1. The resultant product will be amorphous gallium arsenide doped with phosphorus having the stoichiometry GaAs$_{0.995}$ P$_{0.005}$.

This methodology can be extended to incorporate any dopant, in any stoichiometry, in any of the Group IIIA-Group VA compounds described above.

It will be apparent to those skilled in the art having regard to this disclosure that other modifications of this invention beyond those embodiments specifically described here may be made without departing from the spirit of the invention. Accordingly, such modifications are considered within the scope of the invention as limited solely by the appended claims.

What is claimed is:

1. A method of synthesizing amorphous Group IIIA-Group VA compounds comprising the steps of:
    (a) mixing equimolar amounts of a tris(trialkylsilyl) compound of a Group IIIA element with a halide of a Group VA element in a non-protic, non-active hydrogen containing dried, deoxygenated organic solvent wherein the Group IIIA element is selected from the group consisting of aluminum, boron, gallium, indium, and mixtures thereof and the Group VA element is selected from the group consisting of antimony, arsenic, nitrogen, phosphorus, and mixtures thereof;
    (b) reacting the components of the mixture of step (a) to form an adduct of the general formula:

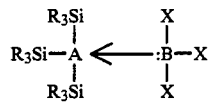

wherein
    R = an alkyl group;
    A = aluminum, boron, gallium, indium, or mixtures thereof;
    B = antimony, arsenic, nitrogen, phosphorus, or mixtures thereof; and
    X = bromine, chlorine, fluorine, or iodine,
thereinafter which is formed a Group IIIA-Group VA compound having the general formula AB and a halide by-product having the general formula R$_3$SiX; and
    (c) removing the R$_3$SiX by-product to recover the AB stoichiometric condensed phase, wherein said phase contains less than about 10% by volume crystallinity.

2. The method of claim 1 wherein the alkyl group is selected from the group consisting of methyl, ethyl, propyl, and butyl groups.

3. The method of claim 2 wherein the alkyl group is a methyl group.

4. The method of claim 1 wherein the Group IIIA element is aluminum, the Group VA halide is NBr$_3$, NCl$_3$, or NI$_3$, and the condensed phase is aluminum nitride.

5. The method of claim 1 wherein the Group IIIA element is aluminum, the Group VA halide is PBr$_3$, PCl$_3$, PF$_3$, or PI$_3$, and the condensed phase is aluminum phosphide.

6. The method of claim 1 wherein the Group IIIA element is boron, the Group VA halide is NBr$_3$, NCl$_3$, or NI$_3$, and the condensed phase is boron nitride.

7. The method of claim wherein the Group IIIA element is boron, the Group VA halide is PBr$_3$, PCl$_3$, PF$_3$, or PI$_3$, and the condensed phase is boron phosphide.

8. The method of claim 1 wherein the Group IIIA element is gallium, the Group VA halide is AsBr$_3$, AsCl$_3$, AsF$_3$, or AsI$_3$, and the condensed phase is gallium arsenide.

9. The method of claim 1 wherein the Group IIIA element is gallium, the Group VA halide is PBr$_3$, PCl$_3$, PF$_3$, or PI$_3$, and the condensed phase is gallium phosphide.

10. The method of claim 1 wherein the Group IIIA element is gallium, the Group VA halide is NBr$_3$, NCl$_3$, or NI$_3$, and the condensed phase is gallium nitride.

11. The method of claim 1 wherein the Group IIIA element is indium, the Group VA halide is PBr$_3$, PCl$_3$, PF$_3$, or PI$_3$, and the condensed phase is indium phosphide.

12. The method of claim 1 wherein the Group IIIA element is indium, the Group VA halide is AsBr$_3$, AsCl$_3$, AsF$_3$, or AsI$_3$, and the condensed phase is indium arsenide.

13. The method of claim 1 wherein the Group IIIA element is indium, the Group VA halide is SbBr$_3$, SbCl$_3$, SbF$_3$, or SbI$_3$, and the condensed phase is indium antimonide.

14. A method of synthesizing amorphous Group IIIA-Group VA compounds comprising the steps of:
   (a) mixing equimolar amounts of a tris-trialkylsilyl) compound of a Group VA element with a halide of a Group IIIA element in a non-protic, non-active hydrogen containing dried, deoxygenated organic solvent wherein the Group VA element is selected from the group consisting of antimony, arsenic, nitrogen, phosphorus, and mixtures thereof and the Group IIIA element is selected from the group consisting of aluminum, boron, gallium, indium, and mixtures thereof;
   (b) reacting the components of the mixture of step (a) to form an adduct of the general formula:

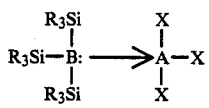

wherein
R=alkyl group;
B=antimony, arsenic, nitrogen, phosphorus or mixtures thereof;
A=aluminum, boron, gallium, indium or mixtures thereof; and
X=bromine, chloride, fluorine or iodine,
thereinafter which is formed a Group IIIA-Group VA compound having the general formula AB and a halide by-product having the general formula R$_3$SiX; and
   (c) removing the R$_3$SiX by-product to recover the AB stoichiometric condensed phase, wherein said phase contains less than about 10% by volume crystallinity.

15. The method of claim 14 wherein the alkyl group is selected from the group consisting of methyl, ethyl, propyl, and butyl groups.

16. The method of claim 15 wherein the alkyl group is a methyl group.

17. The method of claim 14 wherein the Group VA element is arsenic, the Group IIIA halide is GaBr$_3$, GaCl$_3$, GaF$_3$, or GaI$_3$ and the condensed phase is gallium arsenide.

18. The method of claim 14 wherein the Group VA element is phosphorus, the Group IIIA halide is GaBr$_3$, GaCl$_3$, GaF$_3$, or GaI$_3$ and the condensed phase is gallium phosphide.

19. The method of claim 14 wherein the Group VA element is nitrogen, the Group IIIA halide is GaBr$_3$, GaCl$_3$, GaF$_3$, or GaI$_3$ and the condensed phase is gallium nitride.

20. The method of claim 14 wherein the Group VA element is phosphorus, the Group IIIA halide is InBr$_3$, InCl$_3$, InF$_3$, or InI$_3$ and the condensed phase is indium phosphide.

21. The method of claim 14 wherein the Group VA element is arsenic, the Group IIIA halide is InBr$_3$, InCl$_3$, InF$_3$, or InI$_3$ and the condensed phase is indium arsenide.

22. The method of claim 14 wherein the Group VA element is antimony, the Group IIIA halide is InBr$_3$, InCl$_3$, InF$_3$, or InI$_3$ and the condensed phase is indium antimonide.

23. The method of claim 14 wherein the Group VA element is nitrogen, the Group III halide is AlBr$_3$, AlCl$_3$, AlF$_3$, or AlI$_3$ and the condensed phase is aluminum nitride.

24. The method of claim 14 wherein the Group VA element is phosphorus, the Group IIIA halide is AlBr$_3$AlCl$_3$, AlF$_3$, or AlI$_3$ and the condensed phase is aliuminum phosphide.

25. The method of claim 14 wherein the Group VA method is nitrogen, the Group IIIA halide is BBr$_3$, BCl$_3$, BF$_3$, or BI$_3$ and the condensed phase is boron nitride.

26. The method of claim 14 wherein the Group VA element is phosphorus, the Group IIIA halide is BBr$_3$, BCl$_3$, BF$_3$, or BI$_3$ and the condensed phase is boron phosphide.

27. A method of synthesizing amorphous Group IIIA-Group VA compounds comprising the steps of:
   (a) dissolving a tris(trialkylsilyl) compound of a Group IIIA element in a non-protic, non-active hydrogen containing, dried, deoxygenated organic solvent to produce a first solution, wherein the Group IIIA element is selected from the group consisting of aluminum, boron, gallium, indium, and mixtures thereof;
   (b) dissolving a halide of a Group VA element in an inert, dried, deoxygenated organic solvent to produce a seconds solution, wherein the Group VA element is selected from the group consisting of antimony, arsenic, nitrogen, phosphorus, and mixtures thereof;
   (c) mixing said first solution with said second solution wherein a reaction occurs such that a Group IIIA-Group VA compound and a trialkylhalosilane by-product are produced in the organic solvent mixture; and
   (d) removing the trialkylhalosilane by-product and organic solvent mixture to recover the Group IIIA-Group VA condensed phase, wherein said phase contains less than about 10% by volume crystallinity.

28. The method of claim 27 wherein the alkyl group is selected from the group consisting of methyl, ethyl, propyl, and butyl groups.

29. The method of claim 28 wherein the alkyl group is a methyl group.

30. The method of claim 27 wherein the step of removing is by distillation.

31. A method of synthesizing amorphous Group IIIA-Group VA compounds commprising the steps of:
(a) dissolving a tris-(trialkylsilyl) compound of a Group VA element in a non-protic, non-active hydrogen containing dried, deoxygenated organic solvent to produce a first solution, wherein the Group VA element is selected from the group consisting of antimony, arsenic, nitrogen, phosphorus, and mixtures thereof;
(b) dissolving a halide of a Group IIIA element in an inert, dried, deoxygenated organic solvent to produce a second solution, wherein the Group IIIA element is selected from the group consisting of aluminum, boron, gallium, indium, and mixtures thereof;
(c) mixing said first solution with said second solution wherein a reaction occurs such that a Group IIIA-Group VA compound and a trialkylhalosilane by-product are produced in the organic solvent mixture; and
(d) removing the trialkylhalosilane by-product and organic solvent mixture to recover the Group IIIA-Group VA condensed phase, wherein said phase contains less than about 10% by volume crystallinity.

32. The method of claim 31 wherein the alkyl group is selected from the group consisting of methyl, ethyl, propyl, and butyl groups.

33. The method of claim 32 wherein the alkyl group is a methyl group.

34. The method of claim 31 wherein the step of removing is by distillation.

35. The method of claim 2 wherein said solvent is selected from the group consisting of tetrahydrofuran, decalin, dioxane, hexane, octane, benzene, xylene, toluene and mixtures thereof.

36. The method of claim 15 wherein said solvent is selected from the group consisting of tetrahydrofuran, decalin, dioxane, hexane, octane, benzene, xylene, toluene and mixtures thereof.

37. The method of claim 28 wherein said solvent is selected from the group consisting of tetrahydrofuran, decalin, dioxane, hexane, octane, benzene, xylene, toluene and mixtures thereof.

38. The method of claim 32 wherein said solvent is selected from the group consisting of tetrahydrofuran, decalin, dioxane, hexane, octane, benzene, xylene, toluene and mixtures thereof.

* * * * *

UNITED STATES PATENT AND TRADEMARK OFFICE
CERTIFICATE OF CORRECTION

PATENT NO. : 4,798,701

DATED : January 17, 1989

INVENTOR(S) : Lawrence D. David

It is certified that error appears in the above-identified patent and that said Letters Patent is hereby corrected as shown below:

Column 8, line 67, claim 7, "7. The method of claim wherein the Group IIIA" should read -- 7. The method of claim 1 wherein the Group IIIA --.

Signed and Sealed this

Eighteenth Day of July, 1989

Attest:

DONALD J. QUIGG

Attesting Officer

Commissioner of Patents and Trademarks